United States Patent
Andre et al.

(10) Patent No.: US 6,974,679 B2
(45) Date of Patent: *Dec. 13, 2005

(54) SUPPORT WITH COLLAGEN BASE FOR TISSUE ENGINEERING AND MANUFACTURE OF BIOMATERIALS

(75) Inventors: Valerie Andre, Ampuis (FR); Nabil Abdul Malak, Caluire (FR); Alain Huc, Ste. Foy les Lyon (FR)

(73) Assignee: Coletica, Lyons (FR)

( * ) Notice: Subject to any disclaimer, the term of this patent is extended or adjusted under 35 U.S.C. 154(b) by 239 days.

This patent is subject to a terminal disclaimer.

(21) Appl. No.: 10/364,223

(22) Filed: Feb. 10, 2003

(65) Prior Publication Data

US 2004/0002055 A1 Jan. 1, 2004

Related U.S. Application Data

(63) Continuation-in-part of application No. 09/616,282, filed on Jul. 14, 2000, now Pat. No. 6,541,023, which is a continuation-in-part of application No. 09/616,526, filed on Jul. 14, 2000, now Pat. No. 6,790,454.

(30) Foreign Application Priority Data

May 26, 2000 (FR) .............................................. 00 06743
May 26, 2000 (FR) .............................................. 00 06748

(51) Int. Cl.[7] .............................. C12Q 1/02; C12Q 1/00; C12N 5/00; A61F 13/00
(52) U.S. Cl. .............................. 435/29; 435/4; 435/397; 435/398; 424/422; 424/423; 424/425; 424/484
(58) Field of Search .............................. 435/29, 4, 397, 435/398; 424/422, 423, 425, 484

(56) References Cited

U.S. PATENT DOCUMENTS

| | | | |
|---|---|---|---|
| 5,093,474 A | 3/1992 | Grossman et al. | 530/355 |
| 5,166,187 A | 11/1992 | Collombel et al. | 514/21 |
| 5,264,551 A | 11/1993 | Petite et al. | 530/356 |
| 5,273,900 A | 12/1993 | Boyce | 435/240.23 |
| 5,331,092 A | 7/1994 | Huc et al. | 530/356 |
| 5,412,076 A | 5/1995 | Gagnieu | 530/356 |
| 5,420,248 A | 5/1995 | Devictor et al. | 530/356 |
| 6,541,023 B1 * | 4/2003 | Andre et al. | 424/422 |
| 6,790,454 B1 * | 9/2004 | Abdul Malak et al. | 424/422 |

FOREIGN PATENT DOCUMENTS

| | | |
|---|---|---|
| DE | 226 153 A3 | 8/1995 |
| EP | 0 602 297 A1 | 6/1994 |

(Continued)

OTHER PUBLICATIONS

Yeh et al. "A novel native matrix for tissue engineering. Analysis of cell–matrix interaction". Bioartificial Organ Center, PRIT, Taiwan, R.O.C. (1985).

(Continued)

Primary Examiner—Louise N. Leary
(74) Attorney, Agent, or Firm—Merchant & Gould P.C.

(57) ABSTRACT

The invention relates to a method of in vitro testing of the efficacy of a potentially active substance comprising monitoring the effect of said potentially active substance on an artificial skin, comprising a composite product forming a collagen support comprising at least one porous collagen layer covered on at least one side with a collagen membrane component selected from the group consisting of a collagen membrane prepared by compression of a collagen sponge at a pressure of at least about 50 bar and of a collagen membrane comprising a collagen film prepared by drying a collagen gel separately from the porous collagen layer, thereby providing a reliable method for finding new potentially active substances.

50 Claims, 3 Drawing Sheets

FOREIGN PATENT DOCUMENTS

| | | |
|---|---|---|
| EP | 0 686 402 A1 | 12/1995 |
| EP | 0 753 313 A1 | 1/1997 |
| EP | 0753313 | 1/1997 |
| EP | 0 789 074 A1 | 8/1997 |
| FR | 592 603 A | 8/1925 |
| FR | 2 679 779 | 2/1993 |
| FR | 2 724 563 | 3/1996 |
| FR | 2 783 429 | 3/2000 |
| GB | 2 238 051 A | 5/1991 |
| JP | 07075566 | 3/1995 |
| WO | WO 89/08467 | 9/1989 |
| WO | WO 90/12055 | 10/1990 |
| WO | WO 91/16010 | 10/1991 |
| WO | WO 95/17428 | 6/1995 |
| WO | WO 96/08277 A1 | 3/1996 |
| WO | WO 96/08277 | 3/1996 |
| WO | WO 97/20569 | 6/1997 |
| WO | WO 99/19005 A | 4/1999 |

OTHER PUBLICATIONS

Yeh et al. "A Novel Native Matrix for Tissue Engineering. Analysis of Cell–Matrix Interaction". Faseb Journal, vol. 14, No. 4, Mar. 15, 2000.

Derwent accession No. 1995–151478 & JP 07 075566 A, Marino Forum 21 SH, Mar. 20, 1995.

Wang et al. "Collagen Fibres with Improved Strength for the Repair of Soft Tissue Injuries". Biomaterials, vol. 15, No. 7, (1994): pp. 507–512.

Giraud–Guille et al. "Structural Aspects of Fish Skin Collagen whichh Forms Ordered Arrays via Liquid Crystalline States". Biomaterials, vo. 21, No. 9 (May 2000): pp. 899–906.

Chemical Abstracts, vol. 112, No. 8. Skrodzki et al. "Manufacture of aqueous collagen–containing solutions from fish skin," Feb. 18, 1990, XP–002127982.

Josephson et al. "Bisulfite Suppression of Fish Aromas," *Journal of Food Science*, vol. 48, (1983): pp. 1064–1067. XP–002127981.

Patent abstracts of Japan, vol. 15, No. 275, JP 03–094633 (Ishiwatari), Apr. 19, 1991.

Boyce et al. "Structure of a Collagen–GAC Dermal Skin Substitute Optimized for Cultured Human Epidermal Keratinocytes". *Journal of Biomedical Materials Research*, vol. 22, 939–957 (1988).

\* cited by examiner

INVENTION

SUPPORT WITH COLLAGEN BASE FOR TISSUE ENGINEERING AND MANUFACTURE OF BIOMATERIALS

This application is a Continuation-in-part of application Ser. No. 09/616,282, filed 14 Jul. 2000, now U.S. Pat. No. 6,541,023, which claims priority from French application Ser. No. 00 06748, filed 26 May 2000, and is a Continuation-in-part of application Ser. No. 09/616,526, filed 14 Jul. 2000, now U.S. Pat. No. 6,790,454, which claims priority from French application Ser. No. 00 06743, filed 26 May 2000.

The invention relates to a support with collagen base for tissue engineering and manufacture of biomaterials and to different methods including a method of in vitro testing of the efficacy of a potentially active substance using such a support.

DISCUSSION OF THE PRIOR ART

For many years collagen has proved to be an irreplaceable substrate for the production of artificial tissues containing living cells.

The biomaterials obtained are increasingly used in the field of pharmaceutics and they appear to have a very promising future for the preparation of injured connective tissues or for gene therapy by allowing the introduction and survival of modified cells in a living organism.

Furthermore, for "in vitro" tests, the cosmetic and dermopharmaceutical industries are increasingly using reconstructed skin, especially since animal tests are used less and less in these disciplines.

It is for this reason that several research teams throughout the world have been endeavoring to develop collagen-based supports for the production of living artificial tissues such as skin, cartilage, bone, tendon or reconstructed cornea, so these novel biomaterials have numerous fields of application.

It should be noted that the principal studies carried out in the field covered by the invention are attributable mainly to the following teams: Yannas I., Collombel C., Tinois E., Boyce S., Eisenberg H., Bell E., Kuroyanagi Y., Maruguchi T., Hanthamrongwit M., Auger F. A. and Osborne C. S.; cf. U.S. Pat. No. 5,273,900, for example.

All these researchers use of either gels, or of collagen sponges, these last being obtained by freeze-drying (lyophilization).

It is known by document WO 99/19005 a membrane multi-layer including a layer of collagen layer with prevalence out of collagen II having a sponge texture covered on at least a face and preferably on the two faces, of at least a barrier layer having a closed texture, relatively impermeable.

It arises from the text that the barrier layer is consisted a natural animal membrane (see page 7, lines 23 to 32 and page 8, lines 10 to 30).

This barrier layer aims to prevent the penetration and thus the growth of native tissue cells because this membrane is dedicated to the reconstruction of the bone or especially of the cartilage, so that it is necessary to use, as material prevailing of its porous layer, collagen II obtained from cartilage, preferably from hyaline cartilage of pig (see page 7, lines 14–16).

It should be noted that the cells of cartilage or the chondrocytes have a speed of multiplication or of regeneration much slower than the regeneration speed of the cells of soft tissues such as the fibroblasts and, thus, it is necessary to insulate them to enable them to grow while avoiding being invaded by the cells with fast growth of soft tissues. This document ends in this solution by using a barrier layer tight to the cells which protects the growth of the collagen II cells which support the growth of the chondrocytes (see page 2, lines 15 to 20).

Within the framework of this further described invention, it is initially prepared a bi-layer material of which each layer is able to allow the growth of human living cells, which constitutes an unobvious and completely unexpected solution compared to the state of the art.

The document WO 96/08277 relates to the use of a collagenic membrane as prosthesis of peritoneal regeneration, constituting a prior invention of the same applicant. In this document, a preferred embodiment is a mixed membrane comprising a collagen sponge on which collagen gel was stuck, the membrane being obtained by drying the collagen gel in a nontoxic gaseous fluid, see in particular example II, pages 12 and 13 of this PCT application.

However, in example II, it arises that the obtained sponge is compressed during 15 seconds under a pressure of 150 bars and that the mixed membrane is formed by laying down a collagen gel at 1% collagen on this compressed sponge, this gel being then dried at ambient air.

According to the sponge compression obtained during 15 seconds under a pressure of 150 bars, the obtained mixed membrane is in fact produced starting from two primarily compact layers, which constitutes a structure different from that object of this invention. In addition, in the case of this invention, it was discovered in an unexpected way that the claimed bi-layered structure was compatible with a seeding of at least a layer with human living cells, by allowing their conservation, like their multiplication.

It should be noted that the document FR 2 679 778 constitutes another still prior invention of the same applicant.

Document EP 0 686 402 still constitutes a prior document of the same applicant relating to an anti-adherence post-operative collagenic membrane comprising two layers, a support containing collagen completely covered of a layer of gelatine, the mixture being in a freeze-dried state. It should be noted that here the critical purpose of the gelatine layer is to carry out an effect of gluing of the membrane avoiding adherences and the gelatine has a fast resorption by dissolution at 37° C. in the presence of cells.

Document EP 0 789 074 of L'OREAL relates to an equivalent of skins including the Langerhans cells.

It should be noted that in this application, the described support itself on column 4, page 3, is an unspecified support of prior art. It can be formed by mixed collagen/fibroblaste lattices, a dermis beforehand de-epidermized, an artificial membrane, a subcutaneous substitute containing collagen, a plastic or any other support compatible with cellular viability (column 4, lines 3 to 12).

This document is different from this invention insofar as it uses a dermis obtained by delamination of a skin, covered with a mixture of human keratinocytes previously separated according to a traditional method, mixed with human melanocytes also previously separated according to a known method and which are then submitted to a Co-culture. This document does not foresee a compact layer as laid down within the framework of this invention and which can be seeded with human living cells, combined in a critical way with a porous underlayer which is clearly different from a de-epidermized dermis.

Lastly, document WO 91/16010 describes equivalents of living skin composites first of all consisting in buying in the trade a bovine collagen sponge membrane which is inoculated with fibroblasts cells (see page 8, third and fourth paragraphs).

After incubation, the sponge is reversed and the upper surface is laminated with nonporous collagen which can be treated with pepsin (see page 8 last paragraph) which is in general bovine collagen. It is indicated that the purpose of the treatment with pepsin is to remove the telopeptides (page 9, the first four lines). The pH of the collagen solution is adjusted to a neutral pH, which allows collagen to precipitate. Collagen forms a layer of thin film on the sponge and the whole is cultivated at 37° C. during 60 minutes (page 9, last sentence of the first paragraph).

Then, cultivated keratinocytes are inoculated on the laminated layer and a new is culture still carried out at pH 7.2 and at 35° C. during 10 days.

Within the framework of this invention, as it results from the following description, the bi-layered structure is formed initially and is made up in a critical way of a collagen sponge covered of a compact layer, this compact layer providing unexpected technical effects as given in the following description.

The main difficulties to be overcome in the production of supports for the production of living artificial tissues are as follows: good mechanical strength, low sensitivity to temperatures around 37° C., biological properties favorable to cell development and metabolism, low susceptibility to enzymatic degradation and, finally, for certain applications and particularly reconstructed skin, preferably the presence of a bilayer structure in which one of the layers is as compact as possible and the other is porous.

The researches carried out hitherto have not provided collagen supports which satisfactorily comply with all the constraints listed above.

PURPOSES AND OBJECTS OF THE INVENTION

The object of the present invention is to solve these problems which have remained shelved from both the technical and industrial points of view.

The present invention makes it possible to solve all these technical problems in a particularly simple, inexpensive manner applicable to the industrial scale, particularly in cosmetics, dermopharmaceutics or pharmaceutics.

DETAILED DESCRIPTION OF THE INVENTION

According to a first feature, the present invention provides a novel composite product forming a collagen support comprising at least one porous collagen layer covered on at least one side with an essentially compact collagen membrane consisting either of a collagen film prepared by drying a collagen gel, preferably in air or a gaseous fluid, or of a highly compressed collagen sponge.

According to yet another advantageous characteristic of the composite product of the invention, the collagen sponge is compressed at a pressure of at least about 50 bar, equivalent to about $50.10^5$ Pascals (Pa), and preferably of between 50 bar ($50.10^5$ Pa) and 200 bar ($200.10^5$ Pa), this compression optionally taking place at a temperature of between 20 and 80° C. and preferably of between 40° C. and 60° C.

According to one advantageous characteristic of this composite product, the collagen product is selected from collagen and a mixture of collagen with a polysaccharide, particularly a glycosaminoglycan, chitosan or a derivative thereof, cellulose or a derivative thereof, dextran or a derivative thereof, an alginate or a derivative thereof, or a carrageenan.

According to another advantageous characteristic of this composite product, at least one of the two layers of the latter, i.e. the porous layer and the essentially compact membrane, comprises normal, genetically modified or malignant living cells originating particularly from young or elderly subjects.

In one advantageous variant, the living cells are selected from the group consisting of fibroblasts, keratinocytes, melanocytes, Langerhans' cells originating from the blood, endothelial cells originating from the blood, blood cells, particularly macrophages or lymphocytes, adipocytes, sebocytes, chondrocytes, osteocytes, osteoblasts, Merkel's cells originating from the blood and dendritic cells, said cells being normal, genetically modified or malignant.

According to yet another advantageous characteristic, the composite product contains normal, genetically modified or malignant fibroblasts in the porous layer and normal, genetically modified or malignant living cells on the surface of the compact membrane, said cells being selected particularly from keratinocytes, melanocytes, Merkel's cells originating from the blood, Langerhans' cells originating from the blood, sebocytes, cells originating from the blood, nerve cells and dendritic cells.

In yet another advantageous embodiment of the invention, it can be of particular value to prepare either "young" reconstructed skin using cells taken substantially exclusively from young subjects, or "aged" reconstructed skin obtained from cells taken substantially exclusively from elderly subjects. These models will make it possible to improve our knowledge of the skin ageing process and study the influence of active agents on this process.

In yet another advantageous embodiment of the invention, the essentially compact membrane is prepared prior to combination with the porous layer, preferably comprising a collagen sponge, in particular by preparing the membrane and depositing it on a collagen gel before the whole is frozen and lyophilized to give said composite product.

In yet another embodiment of the composite product according to the invention, the collagen sponge and/or the collagen film and/or the collagen membrane of said product comprise collagen of mammalian origin, particularly of bovine origin.

According to still another advantageous embodiment of the composite product according to the present invention, the collagenic sponge and/or the collagenic film and/or collagenic membrane, includes collagen of marine origin, preferably resulting from teleost fish skins, more particularly from fishes presenting non-pigmented skin areas, even more particularly from flat fishes, still better those which are fished in an industrial way, such as for example the sole, the dab, the turbot, the brill, the non-pigmented ventral skins of which can easily be separated by cutting-up. The preferred fish skin as source of extraction of collagen usable according to the present invention is the skin of sole. The preparation of collagen starting from fish skins is in particular described in the preceding document of applicant EP 0 592 586=U.S. Pat. No. 5,420,248 to which the skilled person in the art will be able to refer. It is particularly unexpected that such a collagenic sponge and/or a collagenic film and/or a collagenic membrane obtained starting from collagen of marine origin, preferably of teleost fishes, can be biocompatible with human living cells used for the manufacture of reconstructed skins and that these human living cells can not only remain alive but also be able to multiply.

According to another advantageous embodiment of the invention, the collagen of mammalian origin, in particular of bovine origin, or preferably of marine origin, in particular of teleost fish skins can be either crosslinked chemically, or by physical crosslinking as that will be described further within the framework of the manufacturing process. It is particularly unexpected that such a crosslinking can be used within the framework of the manufacturing of a biocompatible biomaterial with human cells which are used in the foregoing process for the manufacture of reconstructed skins.

By "biocompatible", it is meant within the framework of this invention that the biomaterial is not toxic toward the human living cells and that it allows also their growth or multiplication. It should be noted that the crosslinking has generally the effect to make material nonbiocompatible, therefore toxic for the living cells and cannot then allow their growth.

In yet another advantageous embodiment of the composite product according to the invention, at least one of the two layers of said product is produced from a collagen gel containing a mixture of soluble collagen and insoluble collagen, for example in the form of fibers.

In the case of the composite product according to the invention, the collagen can be type I and/or type III collagen.

According to a second feature, the present invention also covers a process for the manufacture of a composite product comprising at least one porous collagen layer covered on at least one side with an essentially compact collagen membrane, wherein:

a) first of all the essentially compact collagen membrane is prepared either by drying a first collagen gel, preferably in air or with the aid of a gaseous fluid, or by compressing a collagen sponge obtained by the freezing-lyophilization of a collagen gel;

b) a second collagen gel is prepared separately;

c) either the essentially compact membrane is deposited on the second collagen gel, or the second collagen gel is poured onto the essentially compact membrane; and finally d) the whole is frozen-lyophilized to give said composite product.

In one advantageous variant of this process, the collagen sponge used to prepare the compact membrane is compressed at a pressure of at least 50 bar (about $50.10^5$ Pa) and preferably of between 50 bar ($50.10^5$ Pa) and 200 bar ($200.10^5$ Pa).

The compression step advantageously takes place at a temperature of between 20 and 80° C. and preferably of between 40° C. and 60° C.

In another advantageous embodiment of this process, the collagen sponge and/or the collagen film and/or the collagen membrane are prepared using either collagen or a mixture of collagen with a polysaccharide, particularly a glycosaminoglycan, chitosan or a derivative thereof, cellulose or a derivative thereof, dextran or a derivative thereof, an alginate or a derivative thereof, or a carrageenan.

In another variant of the process, at least one of the two layers, or both layers, are crosslinked.

In one advantageous variant, the above-mentioned crosslinking is a physical crosslinking, particularly a thermal dehydration under vacuum, or TDH, or a chemical crosslinking, particularly with diphenylphosphorylazide, or DPPA, with an aldehyde such as glutaraldehyde, with carbodiimide or with succinimide.

In another advantageous variant of this process, a compound which favors cell development, particularly a growth factor and especially a cytokine or a chemokine, is added during manufacture.

In another advantageous embodiment of the process according to the invention, provision is made for a step for the introduction of normal, genetically modified or malignant living cells into at least one of the two layers.

In one advantageous variant, said living cells are selected from the group consisting of fibroblasts, keratinocytes, melanocytes, Langerhans' cells originating from the blood, endothelial cells originating from the blood, blood cells, particularly macrophages or lymphocytes, chondrocytes, osteocytes, particularly osteoblasts, Merkel's cells originating from the blood, sebocytes, adipocytes, nerve cells, and dendritic cells, and any combination thereof. Said cells may be normal, genetically modified or malignant.

In one particularly advantageous embodiment of the invention, the process comprises introducing fibroblasts into the porous layer.

In a more preferred embodiment of the invention, the process comprises depositing living cells on the surface of the compact membrane, said cells being selected particularly from keratinocytes, melanocytes, Merkel's cells originating from the blood, Langerhans' cells originating from the blood, sebocytes, cells originating from the blood, nerve cells and dendritic cells.

In one variant of the process of the invention, the living cells are provided either by the sequential culture or by the concomitant culture of the different types of cells, these cells originating from culture or biopsy.

According to a third feature, the present invention also covers the use of the composite product forming a collagen support as defined above, or as obtained by the process defined above, or as resulting from the following description relating especially to the Examples, for which every characteristic which appears to be novel compared with any state of the art is claimed as such in its function and in its generality, for the manufacture of artificial skin intended especially for performing in vitro tests on the efficacy of a potentially active substance or for reconstructing damaged areas of skin in vivo.

According to one advantageous characteristic, the artificial skin can be obtained either substantially exclusively from young cells or substantially exclusively from aged cells, in particular for studying the tissue ageing process, especially the skin ageing process, and optionally for testing the efficacy of active principles on this process.

Thus it is seen that the invention provides a solution to the above-mentioned technical problems.

To obtain the strongest collagen materials, the inventors carried out more particularly the process described in U.S. Pat. No. 5,331,092 granted on 19 Jul. 1994. This technique affords a mixture of soluble and insoluble type I and type III native collagens which are very strong from the mechanical point of view and very resistant to enzymatic digestion. These last two characteristics may optionally be improved by any crosslinking technique or by the addition of substances which interact strongly with collagen and do not exhibit toxicity towards the cells. Furthermore, this collagen production process makes it possible virtually to eliminate the risk of biological contamination due to bacteria, viruses or prions.

For the case of supports intended for obtaining reconstructed skin, the inventors came to the idea of preparing bilayer materials by producing firstly the more compact layer and then the porous sponge. This methodology has the advantage of resulting in a much more compact surface layer than all those described hitherto. In particular, sponges compacted by high compression, or films, can therefore be fixed to porous matrices.

The use of the supports described above for tissue engineering applications involves the inoculation of living or genetically modified cells, it being possible for the cells to develop either inside the collagen support or on its surface.

The reconstructed living tissues obtained in this way can be used in numerous cosmetic, dermopharmaceutical or pharmaceutical applications as:

- "in vitro" models for simulating the effects of ingredients on cell metabolisms for the purpose of evaluating the efficacy and toxicity of raw materials or more complex formulations;
- reconstructed tissues capable of overcoming the deficiencies of damaged tissues: skin, cartilage, bone, tendon, cornea; or
- living implants containing modified cells capable of overcoming certain deficiencies of the organism, particularly in the field of gene therapy.

Other objects, characteristics and advantages of the invention will become clearly apparent from the following explanatory description referring to various Examples of the invention, which are given simply by way of illustration and cannot therefore in any way limit the scope of the invention. As indicated previously, any characteristic in the Examples which appears to be novel compared with any state of the art is claimed in its function and in its generality, independently of the context of the Example. Moreover, Examples 6 to 13 constitute currently preferred embodiments of the composite products according to the invention which form a collagen support. Example 14 refers to comparative tests demonstrating the value of the composite products according to the invention as collagen supports for the manufacture of artificial skin intended especially for performing in vitro tests on the efficacy of a potentially active substance or for reconstructing damaged areas of skin in vivo.

EXAMPLE 1 OF THE INVENTION

Figure 1:
FIG. 1 shows a sectional view, after marking by conventional histological staining, of a composite product according to the present invention which has been produced from a porous lower layer of bovine collagen covered on the top side with an essentially compact upper collagen membrane consisting of a collagen film prepared by drying a collagen gel in air under the conditions of Example 6.
Figure 2:
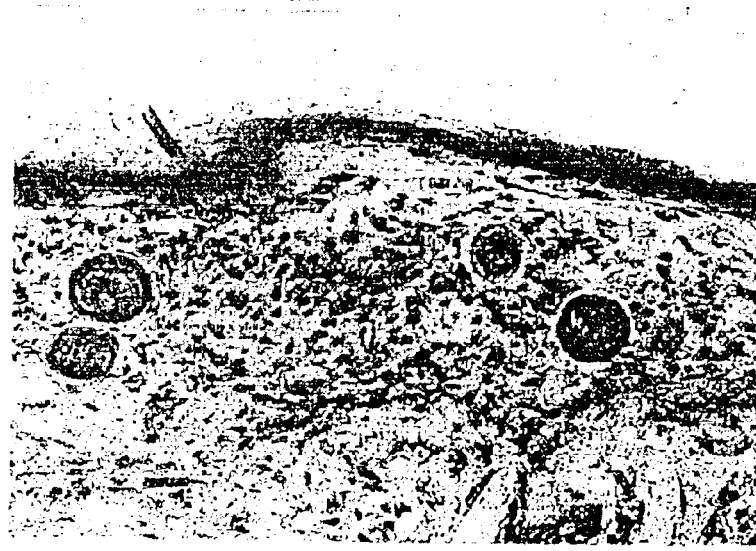
FIG. 2 shows a similar section obtained with a simple porous collagen layer which has been prepared with the same bovine collagen gel, except that it has not been covered, i.e. under the conditions of Example 1, showing the presence of deep inclusions of keratinocytes not limited to the surface.

Preparation of a Porous Collagen Layer of Native Collagen by the Technique of U.S. Pat. No. 5,331,092

A—Preparation of the Native Collagen

A gel is prepared from calf skins which have previously been washed (2 hours) and then depilated with a lime/sulfide mixture (lime: 3.5%, sodium sulfide: 2.5%) at a rate of 400 g of skin (solids content: about 30%) to 250 ml of water. This bath lasts for 30 minutes with rotation at 4 rpm.

The total depilation time is 36 hours.

The skins are then unlimed in a bath containing ammonium chloride (3%) and sodium metabisulfite (0.5%) at a rate of 400 g of skin to 50 ml of bath.

The total duration of this bath is 2 hours thirty minutes.

The salts are removed by two successive washes with water (15 minutes per wash) at a rate of 200 ml of water to 100 g of tissue.

The skins are subsequently ground and then washed by agitation for 1 hour with phosphate buffer of pH 7.8 (0.78 g/l of potassium dihydrogenphosphate and 21.7 g/l of disodium monohydrogenphosphate) at a rate of 5 l buffer/kg ground material. The phosphate is then removed by two successive washes with softened water and then by continuous centrifugation at 4000 rpm (Rousselet centrifuge) at a rate of 5 l of water per kg of ground material.

The ground material is then acidified with 10% acetic acid solution, the amount of acetic acid being 5% based on the collagen; the final molarity is about 0.08 M.

The ground material is then malaxated for one hour to give a paste.

The gel is obtained by continuously passing the paste through a UTL T/-6 ultrasonic treatment apparatus. This gel has a concentration of between 0.7 and 2% of collagen, the proportion of acid-soluble collagen varying from 10 to 20% based on the insoluble collagen.

B—Preparation of the Porous Collagen Layer with the Collagen Gel Obtained as Indicated Above 20 g/cm² of collagen gel (solids content=0.75%) are placed in a lyophilization tray and lyophilized by freezing at −30° C. and then heating at +32° C. The total lyophilization time is 16 hours under a pressure of 400 microbar.

The lyophilizate is crosslinked by a physical method (TDH), the lyophilizate being placed for 10 hours in an oven at 110° C. and 400 microbar of pressure.

EXAMPLE 2 OF THE INVENTION
Preparation of a Porous Collagen Layer Crosslinked with Diphenylphosphorylazide (DPPA) by the Technique Described in European Patent No. 466 829 of 24 Jul. 1996

The collagen lyophilizate is incubated for 24 h in a solution containing 5 to 250 µl DPPA/g collagen in 100 ml of dimethylformamide (DMF). The collagen is then rinsed in 100 ml of DMF to remove the DPPA. The DMF is then removed by rinsing in 100 ml of a borate buffer solution of pH 8.9 (0.04 M sodium tetraborate, 0.04 M boric acid).

The collagen is finally incubated overnight in the same borate buffer, the borate buffer then being removed by continuous rinsing with softened water for 6 h.

EXAMPLE 3 OF THE INVENTION
Preparation of a Porous Collagen Layer Crosslinked with Carbodiimide and N-hydroxysuccinimide The collagen is crosslinked with EDC (ethyldimethylaminopropylcarbodiimide) at a concentration of 0.23 to 0.69 g/g collagen and with NHS (N-hydroxysuccinimide) at a concentration of 0 to 0.42 g/g collagen.

After rinsing with softened water, the collagen is lyophilized again.

EXAMPLE 4 OF THE INVENTION
Preparation of a Porous Collagen Layer Crosslinked with Glutaraldehyde The collagen is crosslinked for 24 to 96 h in a solution containing 0.6 to 1% of GTA at 20° C.

After rinsing with softened water, the collagen is lyophilized again.

EXAMPLE 5 OF THE INVENTION
Porous Collagen Layer Prepared with the Native Collagen of Example 1 in Association with Chitosan and a Glycosaminoglycan as Described in European Patent No. 296078 of 29 May 1991

A solution of 2.5 g of chitosan in 356 ml of water and 1.9 ml of acetic acid, and then a solution containing 1 g of chondroitin 4-sulfate in 400 ml of softened water, are added to 600 g of 1.5% collagen gel. The mixture, which has a pH of about 4.0, is subsequently agitated and then lyophilized.

The sponge obtained is crosslinked by TDH.

EXAMPLE 6 OF THE INVENTION
Porous Collagen Layer Described in Example 1, covered with a Collagen Film A—Preparation of the Film Collagen gel with a solids content of between 0.3 and 0.8% is dried in an oven at 30° C. or under a hood at a rate of 0.5 g gel/cm² tray. 10 to 40% of glycerol can be added to the collagen gel.

The collagen dried under these conditions forms a transparent film.

B—Association of the Film with the Porous Collagen Layer Described Above 0.5 g/cm² of collagen gel of example 1 with a solids content of 0.75% is placed in a lyophilization tray, the collagen film is then deposited on this gel and the whole is lyophilized.

The lyophilizate obtained is crosslinked by TDH.

EXAMPLE 7 OF THE INVENTION
Porous Collagen Layer Prepared with an Acid-Soluble Collagen Gel and Covered with a Collagen Film The process is that indicated in Example 6, the only difference being in the nature of the gel poured onto the film, which consists of acid-soluble collagen prepared by a technique well known to those skilled in the art.

EXAMPLE 8 OF THE INVENTION
Porous Collagen Layer Prepared with an Atelocollagen Gel and Covered with a Collagen Film The process is that indicated in Example 6, the only difference being in the nature of the gel poured onto the film, which consists of atelocollagen, i.e. telopeptide-free collagen prepared by a technique well known to those skilled in the art.

EXAMPLE 9 OF THE INVENTION
Porous Matrix Collagen Layer Consisting of Collagen Associated with Chitosan and a Glycosaminoglycan and Covered with a Collagen Film The process is that indicated in Example 6 except that in this case the gel poured onto the collagen film consists of collagen, chitosan and a glycosaminoglycan. The preparation of this gel is described in Example 5.

EXAMPLE 10 OF THE INVENTION
All the porous matrices described above, covered with a collagen film, can be crosslinked by the techniques described in Examples 2, 3 and 4.

EXAMPLE 11 OF THE INVENTION
Porous Matrix of Collagen Only, Described in Example 1, Covered with a Compressed Collagen Sponge A—Preparation of the Compressed Sponge Collagen gel prepared as in Example 1, with a solids content of between 0.3 and 1.5%, is lyophilized to give a sponge weighing between 0.5 and 2 g/cm².

The lyophilizate is compressed for 5 to 60 seconds at a temperature of between 20 and 60° C. and a pressure of between 50 and 200 bar (50 to $200.10^5$ Pa).

B—Association of the Compressed Sponge with the Porous Matrix

The collagen gel described in Example 1 is deposited in a lyophilization tray at a rate of 0.5 g per cm². The compressed sponge is then deposited on this gel and the whole is lyophilized to give a porous collagen sponge covered with a compressed collagen sponge. The whole is crosslinked by TDH as described in Example 1.

EXAMPLE 12 OF THE INVENTION
Porous Matrix Consisting of Collagen, Chitosan and Glycosaminoglycan, as Described in Example 5, Covered with Compressed Sponge The collagen, chitosan and glycosaminoglycan gel prepared by the process of Example 5 is deposited in a lyophilization tray at a rate of 0.5 g per cm², the compressed sponge is then deposited on this gel and the whole is lyophilized. The lyophilizate is then crosslinked by TDH as described in Example 1.

EXAMPLE 13 OF THE INVENTION
All the porous matrices described above, covered with a compressed collagen sponge, can be crosslinked by the techniques described in Examples 2, 3 and 4.

EXAMPLE 14 OF THE INVENTION
Reconstructed Skin Prepared Either with the Aid of the DPPA-Crosslinked Porous Matrix Described in Example 2, or with the Aid of the DPPA-Crosslinked Porous Matrix of Example 2 Covered with a Compressed Collagen Sponge, the Whole being Crosslinked with DPPA, According to Example 13, In Order to Allow a Comparison to be Made between a Composite Product Comprising a Porous Collagen Layer covered with an Essentially Compact Membrane According to the Invention and a Product Comprising a Porous Collagen Layer Only, with no Covering Preparation of Reconstructed Skin a) Culture of Normal Human Fibroblasts Normal human fibroblasts taken arbitrarily from elderly or young subjects are used; they are recovered and developed in a manner conventional to those skilled in the art for recovery between the sixth and tenth passages.

Inoculation is carried out at a rate of 250,000 cells per $cm^2$ of porous matrix, the latter being either the comparison product comprising only the DPPA-crosslinked porous matrix of Example 2, or the composite product according to the invention comprising the DPPA-crosslinked porous matrix of Example 2 covered with a compressed collagen sponge, the whole being crosslinked with DPPA, according to Example 13.

The culture medium is composed of DMEM/HAM F12 50/50 (v/v) supplemented with 10% by weight of fetal calf serum, 100 IU/ml of penicillin, 25 µg/ml of gentamycin, 1 µg/ml of amphotericin B and 50 µg/ml of vitamin C.

Culture is carried out for three weeks, the medium being changed three times a week.

b) Culture of Normal Human Keratinocytes

Normal human keratinocytes obtained arbitrarily from young or elderly subjects are then cultured; they are recovered and cultivated by the culture techniques well known to those skilled in the art for recovery between the first and third passages.

Inoculation is carried out at a rate of 250,000 cells per $cm^2$ of surface, which is either the surface of the DPPA-crosslinked porous matrix of Example 2, or the surface of the composite product according to the invention comprising the DPPA-crosslinked porous matrix of Example 2 covered with a compressed collagen sponge, the whole being crosslinked with DPPA, according to Example 13, in which case the keratinocytes are inoculated onto the surface of the essentially compact collagen membrane.

The culture of these products, comprising an inoculation of both fibroblasts and keratinocytes, takes place in a Green's medium composed of:
  DMEM supplemented with:
  30% of HAM F12,
  10% of fetal calf serum,
  100 IU/ml of penicillin,
  100 µg/ml of streptomycin,
  1 µg/ml of amphotericin B,
  2 µmol/ml of L-glutamine,
  10 ng/ml of EGF (Epidermal Growth Factor),
  0.12 IU/ml of insulin commercially available under the trade mark UMULINE®,
  400 ng/ml of hydrocortisone,
  $10^{-12}$ mol/ml of cholera toxin,
  5 µg/ml of transferrin,
  $2.10^{-9}$ M triiodothyronine,
  $1.8.10^{-7}$ mol/ml of adenine,
  50 µg/ml of vitamin C.

This culture is carried out for one week, the media being changed every day.

c) Culture of the Composite Product According to the Invention and the Comparative Non-Covered Porous Layer After the culture of step b) has been carried out for one week with the media being changed every day, the surface layer containing the keratinocytes is caused to emerge at the air-liquid interface, while the layer containing the fibroblasts remains immersed, and culture is then carried out for three weeks in an emersion medium composed of:
  DMEM supplemented with:
  10% of fetal calf serum,
  100 IU/ml of penicillin,
  100 µg/ml of streptomycin,
  1 µg/ml of amphotericin B,
  2 µmol/ml of L-glutamine,
  10 ng/ml of EGF,
  0.12 IU/ml of insulin of trade mark UMULINE®,
  400 ng/ml of hydrocortisone,
  50 µg/ml of vitamin C.

The total culture time of 7 weeks resulting from steps a) to c) gives a reconstructed skin composed of a reconstructed dermis, the fibroblasts having colonized the three-dimensional collagen matrix, said dermis being covered with a multilayer epidermis.

The dermo-epidermal interface shows the presence of a basal membrane in which it is possible to identify the presence of laminin-1, laminin-5, type IV collagen and type VII collagen by immunolabeling.

Thus, after three weeks of preparation of the dermis equivalent, covering of the porous matrices with an essentially compact layer to give a composite product according to the invention affords a greater quantity of fibroblasts on the surface of the collagen matrices before epidermization.

In the case of a porous matrix only, i.e. with no covering, if the surface layer of fibroblasts is not completely contiguous, keratinocytes can infiltrate the underlying dermis equivalent and form islets of keratinocytes, which are totally abnormal features.

Thus it is seen that the invention, which uses more compact layers than those previously available for use in the prior art, provides better security against the penetration of keratinocytes.

It is pointed out that the abbreviation DMEM in the description denotes Dulbecco Modified Eagle's Medium.

EXAMPLE 15 OF THE INVENTION

Study Comparing Skin Reconstructed from Cells of Young Donors and Skin Reconstructed from Cells of Elderly Donors with the Composite Products According to the Present Invention in Order to Measure the Efficacy of Active Principles on the Production of Laminins The procedure in this Example is essentially as described in Example 14 as regards the cultures, using the same composite product according to the present invention comprising a DPPA-crosslinked porous collagen layer or matrix described in Example 2, covered with a compressed collagen sponge, the whole being crosslinked with DPPA, according to Example 13. The procedure is as follows:

1) Preparation of the Reconstructed Skin

Young reconstructed skin was prepared by the procedure described in Example 14 except that the fibroblasts and keratinocytes originated respectively from young donors, i.e. those of between 25 and 35 years of age. Also, aged or mature reconstructed skin was obtained by using fibroblasts or keratinocytes originating from elderly donors of more than 55 years of age.

a) Materials and Method

As indicated in Example 14, step a, porous matrices of the composite product of the invention were first inoculated with normal human dermal fibroblasts originating either from pools of young cells or from pools of mature or aged cells, and culture is carried out for 21 days under the conditions described in Example 14, step a.

b) After the above-mentioned 21 days of culture, epidermal layers prepared separately from keratinocytes originating either from pools of young cells or from pools of mature cells are inoculated onto the surface of the essentially compact collagen membrane of the composite product.

Culture is carried out for 14 days under the conditions described in Example 14b.

2) Quantification of the Laminins

After the 14 days of culture of the fibroblast-keratinocyte composite, the laminins contained in the incubation media of the resulting young or mature reconstructed skin are quantified with the aid of a commercially available ELISA kit (Takara, Japan).

Figure 3:
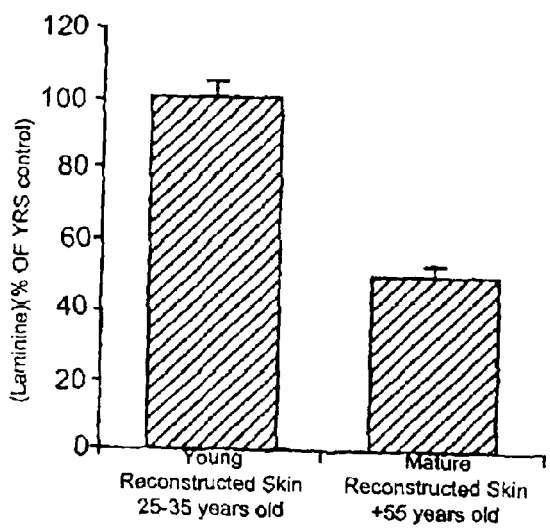
FIG. 3 shows the quantity of laminins present in the reconstructed skin incubation media, respectively for young reconstructed skin obtained from cells taken from donors of 25 to 35 years of age, and for mature or aged reconstructed skin obtained from cells taken from donors of more than 55 years of age, in order to show the influence of the donor's age, the results being expressed in the form of "bars" and the quantity of laminins produced being expressed on the ordinate as a percentage of the control (YRS=young reconstructed skin)

These results are reported in FIG. 3.

FIG. 3 shows that the mature reconstructed skin contains about half as much laminins as the young reconstructed skin (YRS) used as 100% control.

3) Measurement of the Inductive Effect of an Active Principle, Such as a Fermented Malt Extract Marketed by COLETICA Under the Trade Mark BASALINE®, on the Production of Laminins in Young and Mature Reconstructed Skin In this comparative test, the procedure is as described above except in regard to the 14 days of culture with keratinocytes; the young or mature reconstituted skin is maintained in culture for 14 days either in the absence (control) or in the presence of 0.5% by weight of fermented malt extracts commercially available under the trade mark BASALINE®, COLETICA, France.

At the end of the incubation period, as in the above Example, the laminins contained in the incubation media were quantified by ELISA.

Figure 4:
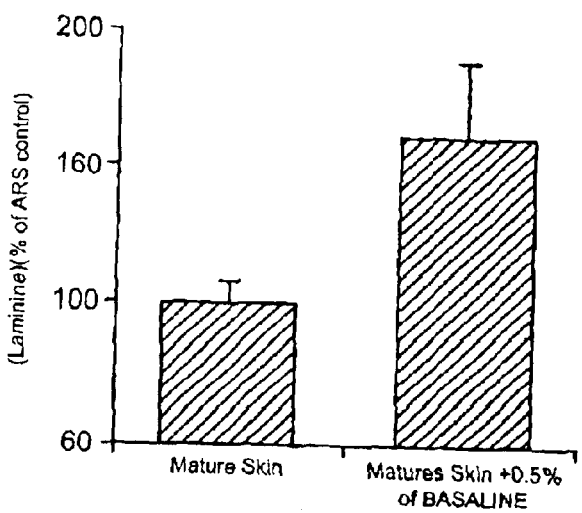
FIG. 4 shows the inductive effect of a fermented malt extract commercially available under the trade mark BASALINE®, COLETICA, France, on the production of laminins in mature reconstructed skin, the quantity of laminins produced again being expressed as a percentage of the control.

The results are reported in FIG. 4.

The 100% control consists of the proportion of laminins in Aged Reconstructed Skin, or ARS.

Figure 5:
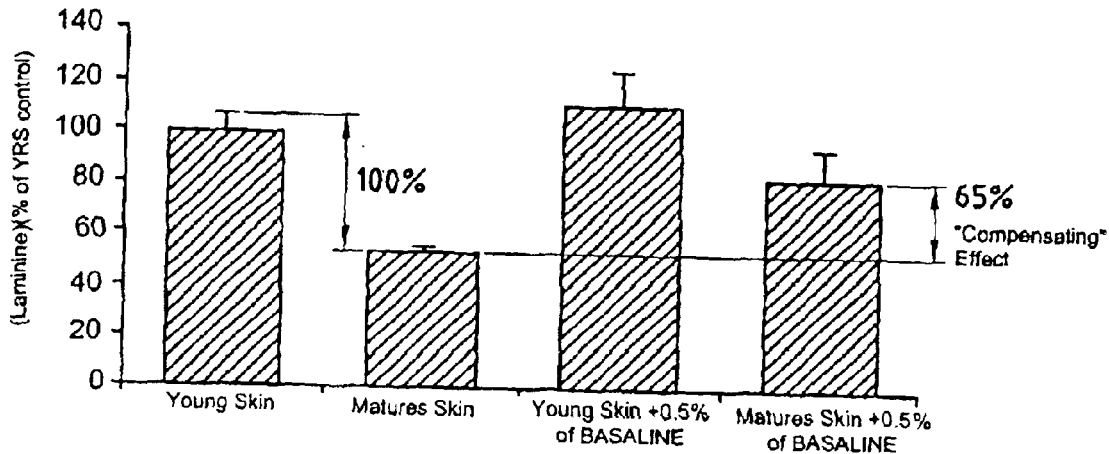
FIG. 5 shows the compensating effect of the same fermented malt extract, or BASALINE®, the quantity of laminins produced being expressed on the ordinate as a percentage of the control.

FIG. 4 shows that the active principle extracted from fermented malt, or BASALINE®, was capable of stimulating laminin production in mature reconstructed skin. Under the same conditions, the active principle extracted from fermented malt, or BASALINE®, does not significantly modify laminin production in young reconstructed skin, as indicated in FIG. 5.

Thus it is seen that the active principle extracted from fermented malt, or BASALINE®, increases laminin production in mature reconstructed skin by 65%.

By the same token, this active principle does not affect the physiological processes involved in the regulation of laminin production in young reconstructed skin.

These experiments made it possible to evaluate the magnitude of the compensating effect of the fermented malt extract, or BASALINE®, defined as the capacity of this active principle to reduce the relative difference observed between laminin production in young reconstituted skin and that in mature reconstituted skin.

FIG. 5 shows that the difference between laminin production in young reconstituted skin and that in mature reconstituted skin can be reduced by 65% when the active principle is used at 0.5%.

EXAMPLE 16

Preparation of a Porous Matrix of Aquatic Native Collagen

The collagen is obtained by the technique of U.S. Pat. No. 5,331,092 granted on 19 Jul. 1994.

A—Preparation of the Aquatic Native Collagen

A collagen gel is prepared from ventral sole skin which is ground and then washed with a phosphate buffer of pH 7.8 having the following composition: 0.78 g/l of potassium dihydrogenphosphate and 21.7 g/l of disodium monohydrogenphosphate. The washing is carried out with agitation for one hour at a rate of 5 of buffer per kg of ground material. The phosphate is then removed by means of two successive washes with softened water, followed by continuous centrifugation at 4000 rpm (Rousselet centrifuge), at a rate of 5 l of water per kg of ground material.

The ground material is then acidified with 0.25 M acetic acid solution at a rate of 1 kg of ground material to 10 l of solution. The gel is then centrifuged at 4000 rpm for 5 min.

The gel to be used consists of the supernatant obtained, which has a collagen concentration of between 0.5 and 2%.

B—Preparation of the Porous Matrix from the Collagen Gel Obtained Above

This gel is poured into a lyophilization tray at a rate of 20 g/cm$^2$. It is then lyophilized after freezing at −30° C. and heating at +32° C.

The total lyophilization time is 16 hours under a pressure of 400 microbar. The matrix obtained is then crosslinked by thermal dehydration (TDH), which consists in heating in an oven at 110° C. under a vacuum of 400 microbar for 16 hours.

EXAMPLE 17

Preparation of a Porous Matrix Crosslinked with Diphenylphosphorylazide (DPPA) by the Technique Described in European patent no. 466 829 of 24 Jul. 1996

The collagen matrix of Example 1 is incubated for 24 h in a solution containing 5 to 250 µl DPPA/g collagen in 100 ml of dimethylformamide (DMF). The collagen is then rinsed in 100 ml of DMF to remove the DPPA. The DMF is then removed by rinsing in 100 ml of a borate buffer solution of pH 8.9 (0.04 M sodium tetraborate, 0.04 M boric acid).

The collagen is finally incubated overnight in the same borate buffer, the borate buffer then being removed by continuous rinsing with softened water for 6 h.

EXAMPLE 18

Preparation of a Porous Matrix Crosslinked with Carbodiimide and N-Hydroxysuccinimide The aquatic collagen matrix of Example 1 is crosslinked with EDC (ethyldimethylaminopropylcarbodiimide) at a concentration of 0.23 to 0.69 g/g collagen and with NHS (N-hydroxysuccinimide) at a concentration of 0.42 g/g collagen.

After rinsing with softened water, the collagen is lyophilized again.

EXAMPLE 19

Preparation of a Porous Matrix Crosslinked with Glutaraldehyde

The porous matrix of aquatic collagen of Example 1 is crosslinked for 24 to 96 h in a solution containing 0.6 to 1% of GTA at 20° C.

After rinsing with softened water, the collagen is lyophilized again.

EXAMPLE 20

Porous Matrix Prepared with the Aquatic Native Collagen of Example 16 in Association with Chitosan and a Glycosaminoglycan as Described in European patent no. 296078 of 29 May 1991

A solution of 2.5 g of chitosan in 356 ml of water and 1.9 ml of acetic acid, and then a solution containing 1 g of chondroitin 4-sulfate in 400 ml of softened water, are added to 600 g of 1.5% collagen gel. The mixture, which has a pH of about 4.0, is subsequently agitated and then lyophilized.

The sponge obtained is crosslinked by TDH.

EXAMPLE 21
Porous Matrix Described in Example 16, Covered with a Collagen Film A—Preparation of the Film The collagen gel, which has a solids content of between 0.3 and 0.8%, is dried in an oven at 30° C. or under a hood at a rate of 0.5 g gel/cm² tray.

10 to 40% of glycerol can be added to the collagen gel.

The collagen dried under these conditions forms a transparent film.

B—Association of the Film with the Porous Matrix Described Above

The aquatic native collagen gel with a solids content of 0.5% to 2% is deposited in a lyophilization tray at a rate of 0.5 g per cm², the collagen film is then deposited on this gel and the whole is lyophilized.

The lyophilizate obtained is crosslinked by TDH.

EXAMPLE 22
Porous Matrix of Collagen Only, Described in Example 16, Covered with a Compressed Collagen Sponge A—Preparation of the Compressed Sponge The collagen gel prepared as in Example 1, with a solids content of between 0.3 and 1.5%, is lyophilized to give a sponge weighing between 0.5 and 2 g/cm².

The lyophilizate is compressed for 5 to 60 seconds at a temperature of between 20 and 60° C. and a pressure of between 50 and 200 bar (50 to $200.10^5$ Pa).

B—Association of the Compressed Sponge with the Porous Matrix

The collagen gel described in Example 1 is deposited in a lyophilization tray at a rate of 0.5 g per cm². The compressed sponge is then deposited on this gel and the whole is lyophilized to give a porous collagen sponge covered with a compressed collagen sponge. The whole is crosslinked by TDH as described in Example 1.

EXAMPLE 23
Porous Matrix Consisting of Collagen, Chitosan and Glycosaminoglycan, as described in Example 20, covered with Compressed Sponge The collagen, chitosan and glycosaminoglycan gel prepared by the process of Example 20 is deposited in a lyophilization tray at a rate of 0.5 g per cm², the compressed sponge is then deposited on this gel and the whole is lyophilized. The lyophilizate is then crosslinked by TDH as described in Example 16.

EXAMPLE 24
All the porous matrices described above, covered with a compressed collagen sponge, can be crosslinked by the techniques described in Examples 17, 18 and 19.

EXAMPLES 25 TO 27

Tests for Comparing the Cell Metabolism of Bovine and Aquatic Collagen Matrices

EXAMPLE 25

Test for Cell Viability of Fibroblasts

I—Preparation of the Dermis Equivalents

For this comparative test, a DPPA-crosslinked aquatic porous matrix according to Example 17 is prepared first.

By way of comparison, a comparative porous matrix called a bovine matrix, also crosslinked with DPPA, is prepared with collagen of bovine origin under the same conditions as those of Example 17.

Normal human fibroblasts, taken from a young donor pool used at the 7th passage, are inoculated into each of the aquatic and bovine matrices at a rate of 250,000 cells per cm² in the case of the proliferation and protein synthesis study, and at a rate of 300,000 cells per cm² in the case of the aquatic and bovine matrices intended for the histological studies.

These aquatic and bovine matrices are cultured in a medium composed of DMEM/HAM F12 in a ratio of 50/50 (v/v) supplemented with 10% of fetal calf serum, 100 IU/ml of penicillin, 25 µg/ml of gentamycin, 1 µg/ml of amphotericin B and 50 µg/ml of vitamin C.

This culture is carried out for 1 month, the culture medium being changed 3 times a week.

II—Analyses Performed

1) Measurement of Cell Viability by Reaction with MTT

1% by weight of MTT (i.e. 3-(4-(dimethylthiazol-2-yl)-2,5-diphenyl-tetrazolium bromide) is added to the culture medium.

Incubation is carried out for 2.5 hours at 37° C.

After this incubation period, the conversion product (formazan blue) is solubilized in DMSO and its optical density is read at 550 nm.

The optical density obtained is proportional to the activity of the succinate dehydrogenases, which are capable of converting the bright yellow tetrazolium salt, MTT, to blue crystals of formazan.

The cell viability was measured after 1, 5, 7 and 22 days and one month of culture.

To determine the mean values, 6 samples were prepared for each matrix.

TABLE I

RESULTS

| Days | Aquatic matrix | Mean standard deviation | Bovine matrix | Mean standard deviation |
|---|---|---|---|---|
| 1 | 487 | 24 | 403 | 40 |
| 5 | 604 | 19 | 393 | 59 |
| 7 | 520 | 56 | 398 | 64 |
| 22 | 608 | 30 | 680 | 40 |

Figure 6:
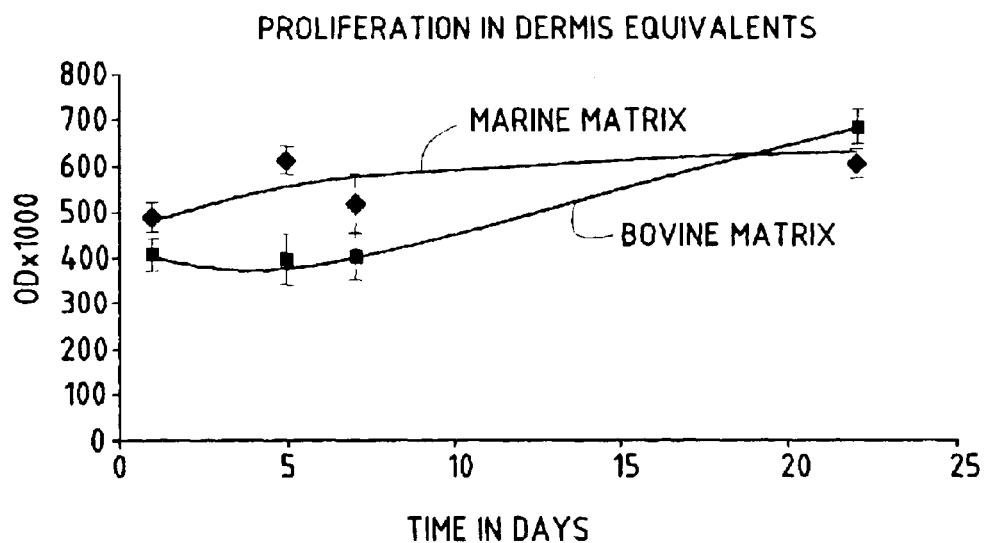
FIG. 6 shows the proliferation of the normal human fibroblasts in dermis equivalent, with the time expressed in day and in abscissa and the optical density×1000 in ordinates with units increasing by 100; the curve with the rhombuses is that which is obtained by using as support a aquatic collagen porous collagen layer, here of fishes, and the curve with squares is obtained with bovine collagen.

These results are also used for the curves in the attached FIG. 6.

It will be noted that the curve with the diamonds is that obtained with the aquatic matrix and the curve with the squares is that obtained with the bovine matrix.

The results show, totally surprisingly, that the aquatic matrix constitutes a support which allows not only the survival of normal human fibroblasts but also the proliferation of these normal human fibroblasts, while at the same time even constituting a much better culture support during the first three weeks.

It can therefore be concluded from these tests that, surprisingly, aquatic collagen is particularly suitable for the production of a tissue engineering support, in particular for applications in vitro and even, above all, in vivo for forming biomaterials containing living cells, particularly and preferably those of human beings.

2) Measurement of Protein Synthesis

The synthesis of proteins secreted over 3 days in a culture medium free of fetal calf serum was evaluated after one month of maturation of the dermis equivalents as obtained after one month of culture under the conditions reported above in the preparation of the dermis equivalents.

The assay is performed by the microBCA method of Pierce.

The cell density was evaluated in parallel by an MTT test under the conditions described above.

The relative protein content corresponds to the protein content per unit of cell density expressed as the optical density, or OD, so that the cell concentration in question is equivalent. The results obtained are shown in Table II below:

TABLE II

RESULTS OF PROTEIN SYNTHESIS

| Collagen of | Aquatic matrix | | Bovine matrix | |
|---|---|---|---|---|
| the support | Mean | * | Mean | * |
| Cell density (OD) | 2.12 | 0.09 | 1.91 | 0.13 |
| Proteins (µg/ml) | 494 | 48 | 499 | 32 |
| Relative protein content | 233 | 18 | 262 | 23 |

*Mean standard deviation

As in Table I, the mean is based on 6 samples.
3) Histology

The dermis equivalents obtained after culture of the aquatic and bovine collagen matrices for 21 days are fixed in 2% paraformaldehyde solution and then post-fixed in osmium tetroxide solution, dehydrated, included in Epon, sectioned and observed by transmission electron microscopy (Jeol 1200) at CMEAGB (Lyon, France).
Conclusions These results indicate a very good colonization of the three-dimensional matrices, whether they be aquatic or bovine. After three weeks of culture, the cell density is equivalent in both types of matrices. However, the aquatic matrix seems to allow a better cell adhesion at the beginning of the experiment, as indicated by the proliferation study in the first week of culture, and hence a better colonization for short culture times.

As far as the protein syntheses are concerned, the fibroblast synthesis capacities (relative protein contents) are also equivalent after one month of culture.

These results indicate that the aquatic collagen matrices developed made it possible to prepare dermis equivalents of good quality, the results obtained with these matrices being comparable to those obtained with bovine collagen matrices.

In transmission electron microscopy, fibroblasts could be observed in the matrices of bovine and aquatic origin. In both types of matrix, the presence of a copious neosynthesized extracellular matrix is noted. The neosynthesized extracellular matrix can be differentiated by virtue of the periodic striation of the fibers of deposited collagen, compared with the collagen clusters forming the three-dimensional matrix of the initial sponge.

EXAMPLE 26

Influence of the Different Types of Crosslinking of the Aquatic Collagen Matrices on the Cell Viability The following tests are carried out in order to study the influence of the different types of crosslinking of the aquatic collagen matrices on the cell viability:
I) Preparation of the Dermis Equivalents
a) Support or Matrix Used Various collagen supports or matrices are prepared using different proportions of collagen in the collagen gel for producing the porous layer or matrix, and optionally using a different crosslinking agent, as follows:
1) Test 1

For this test, a porous matrix in the form of a porous sponge is produced from an aquatic collagen gel prepared from 1.3% by weight of aquatic collagen, which is frozen at −80° C., subjected to standard lyophilization according to Example 17 and then crosslinked with DPPA in a proportion of 250 µl per g of sponge in the dry state.
2) Test 2

For this test, a porous support in the form of an aquatic sponge is prepared from an aquatic collagen gel comprising 0.7% by weight of aquatic collagen, which is frozen at −80° C. and then subjected to standard lyophilization and crosslinked with DPPA in a proportion of 250 µl per g of dry sponge as in test 1.
3) Test 3

For this test, the procedure is as in Test 1 except that the crosslinking is carried out with EDC, according to Example 2, in a proportion of 0.46 g per g of dry sponge.
4) Test 4

A porous support is prepared which comprises a sponge of aquatic collagen obtained from an aquatic collagen gel comprising 1.1% by weight of aquatic collagen, which is frozen at −80° C. and then subjected to standard lyophilization and crosslinked with DPPA in a proportion of 250 µl per g of dry sponge as in Test 2, the difference being in the proportion of 1.1% by weight of aquatic collagen.

In all these tests, the aquatic collagen originates from ventral sole skin as in Example 17.
b) Culture of Fibroblasts on these Matrices Normal human fibroblasts are used as in Example 25, but these are taken at the 8th passage.

Inoculation is carried out at a rate of 275,000 cells per $cm^2$.

The culture medium is composed of DMEM/HAM F12 50/50 (v/v) supplemented with 10% by weight of fetal calf serum, 100 IU/ml of penicillin, 25 µg/ml of gentamycin, 1 µg/ml of amphotericin B and 50 µg/ml of vitamin C.

Culture is carried out for 1 month, the medium being changed 3 times a week.

4 matrices are used for each test so as to take a mean for each type of test and measure the mean standard deviation.
II) Analyses Performed
Measurement of the Cell Viability by Reaction with Alamar Blue (Redox Marker)

Alamar blue is added at a rate of 2% by weight of the culture medium used, at the moment when it is desired to measure the cell viability on a sample taken from the culture medium.

After incubation for 2 h 20 min at 37° C., the fluorescence is read on the basis of an excitation at 530 nm and an emission at 590 nm.

The intensity of the fluorescence obtained is proportional to the metabolic activity of the cells.

The cell viability is measured on 10 samples after 1, 4, 6, 11 and 17 days of culture.

The results are expressed in Table III below.

The results are indicated in international units of fluorescence as a function of time.

TABLE III

| | CELL VIABILITY (IU of fluorescence) | | | | | | | |
|---|---|---|---|---|---|---|---|---|
| Time | TEST 1 | | TEST 2 | | TEST 3 | | TEST 4 | |
| (days) | Mean | SD* | Mean | SD* | Mean | SD* | Mean | SD* |
| 1 | 21,734 | 1184 | 30,535 | 1888 | 25,528 | 6820 | 28,461 | 3805 |
| 4 | 31,611 | 920 | 35,623 | 3544 | 36,404 | 3570 | 45,126 | 2930 |
| 6 | 43,144 | 2500 | 35,244 | 2095 | 37,819 | 4170 | 41,254 | 3396 |
| 11 | 42,808 | 1481 | 38,532 | 2537 | 42,442 | 3112 | 44,508 | 2329 |

TABLE III-continued

| | CELL VIABILITY (IU of fluorescence) | | | | | | | |
|---|---|---|---|---|---|---|---|---|
| Time | TEST 1 | | TEST 2 | | TEST 3 | | TEST 4 | |
| (days) | Mean | SD* | Mean | SD* | Mean | SD* | Mean | SD* |
| 17 | 45,484 | 2426 | 45,094 | 1470 | 43,963 | 8285 | 43,939 | 4521 |
| Order | 1 | | 2 | | 3 | | 4 | |

*Standard deviation

Figure 7:
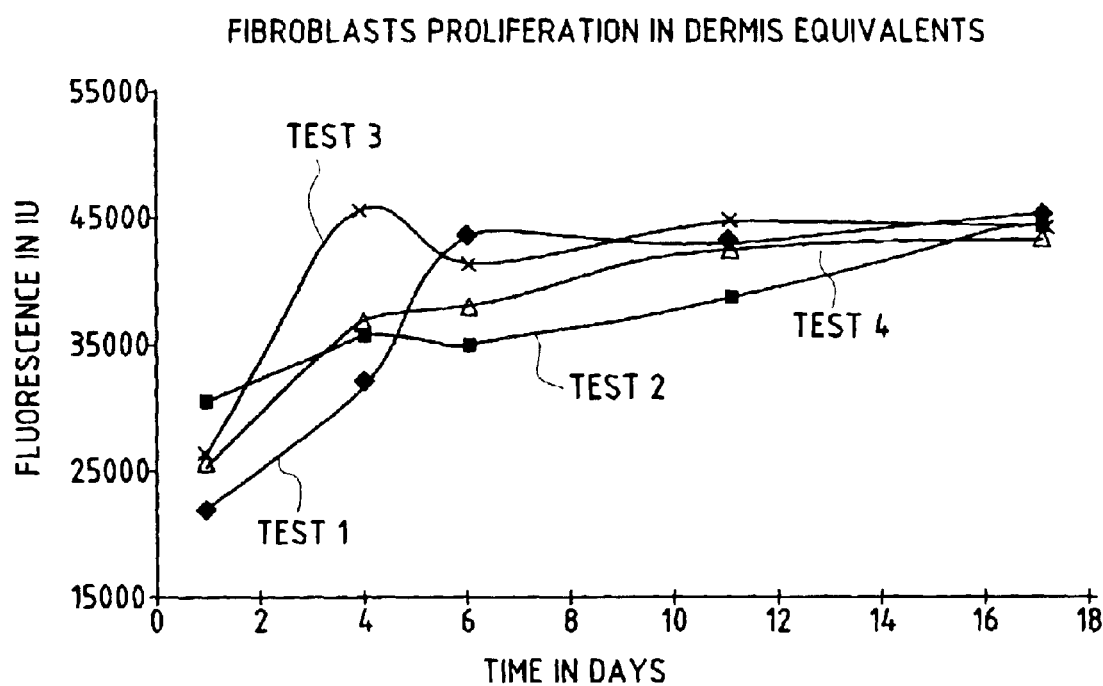
FIG. 7 shows a similar curve of proliferation of fibroblasts in dermis equivalent with the time expressed in day in abscissa and the fluorescence expressed in international unit in ordinates, starting from 15.000 with units increasing by 10.000; the curve with the full rhombuses represents the fluorescence obtained within the framework of test 1; the curve with the square that obtained with test 2; the curve with the empty triangles being obtained with test 3 and finally the curve with the crosses being that obtained with test 4.

The results in Table 3 are also used in the attached FIG. 7.

They show the curves of fibroblast proliferation in dermis equivalents.

The curve with solid diamonds corresponds to Test 1, the curve with solid squares corresponds to Test 2, the curve with triangles corresponds to Test 3 and the curve with crosses corresponds to Test 4.

The time is expressed in days on the abscissa and the fluorescence is expressed in IU with a scale starting at 15,000 and increasing to 55,000 in units of 10,000.

The results allow the following conclusions to be drawn.

Conclusions

The results indicate that the different matrices prepared can permit a good growth of fibroblasts after 17 days of culture. Irrespective of the preparation of the aquatic collagen matrices, the fibroblasts adhere well to their three-dimensional support and divide very rapidly to colonize the matrix.

The proliferation profile varies very slightly from one type of matrix to the other, but the fibroblast density is comparable after 17 days of culture, irrespective of the preparative process.

The different types of crosslinking employed, carried out either with DPPA or with EDC, do not seem to influence the cell renewal. After practically 3 weeks of culture, the stability of the matrices is excellent, there being little digestion and little contraction.

EXAMPLE 27

Test Demonstrating the Advantages of Aquatic Collagen for the Identification and Assay of Neosynthesized Human Collagen This test is similar to that of Example 25 except that histology is carried out with immunolabeling.

The test is performed as follows:

1) Preparation of the Dermis Equivalents

These are the dermis equivalents of Example 25, culture being carried out under the conditions of Example 25.

This culture is therefore carried out for three weeks with the medium being changed three times a week, the normal human fibroblasts having been inoculated at a rate of 300,000 cells per cm$^2$, as indicated in Example 25.

2) Histology a) Conventional Histology

Fixing is effected with paraformaldehyde at a concentration of 4% by weight, after which the material is dehydrated and included in paraffin.

This is followed by the preparation of 7 μm sections and Mallory Haidenhain staining after removal of the paraffin and rehydration.

b) Immunolabeling

Fixing is again effected with 4% by weight of paraformaldehyde, the material is included in Tissue Tek OCT compound, i.e. an inclusion liquid supplied by Miles, Elkhart, Ind., USA, and a 7 μm section is prepared in the cold.

Immunolabeling is performed with the following:

i. a first rabbit anti-human type I collagen antibody (dilution 1/40), and
ii. a second anti-rabbit antibody coupled with FITC (Fluorescein IsoThioCyanate) (dilution 1/160).

DAPI (41,6-diamidino-2-phenylindole dilactate) is used as a counterstain.

3) Results

It is found that supports consisting of an aquatic matrix and a bovine matrix form more or less loose pores to which the fibroblasts adhere.

A greater proportion of fibroblasts is observed on the surface, forming a favorable covering over the dermis equivalent for the production of reconstructed skin. The distribution of the fibroblasts is homogeneous in aquatic and bovine sponges.

In immunolabeling, it is found that the matrix formed of bovine collagen is labeled by the anti-human type I collagen antibody (crossing).

On the other hand, the matrix of aquatic origin is only very weakly labeled by the anti-human collagen antibody.

The use of sponges composed of aquatic collagen therefore favors identification of the neosynthesized extracellular matrix.

These results are explained by Professor Hartmann's studies on the reactions of different antigens to different antibodies, determined by the optical density measurements after immunolabeling which are given below in Table IV, or Hartmann's table:

TABLE IV

| Cross reaction with human, bovine and fish collagen (Elisa) | | | |
|---|---|---|---|
| Antigen | Sole type I collagen | Human type I collagen | Bovine I type collagen |
| Antibody | | | |
| 20111 (225) | | | |
| 1/25 | 190 | > | 815 |
| 1/50 | 210 | > | 548 |
| 1/100 | 73 | 1233 | 234 |
| 1/200 | 43 | 605 | 136 |
| 1/400 | 56 | 326 | 165 |
| 50121 (03) | | | |
| 1/25 | 180 | 1550 | > |
| 1/50 | 130 | 1094 | > |
| 1/100 | 158 | 536 | > |
| 1/200 | 96 | 305 | 967 |
| 1/400 | 109 | 215 | 728 |
| 50171 (01) | | | |
| 1/25 | 1880 | 64 | 73 |
| 1/50 | 1043 | 193 | 32 |
| 1/100 | 571 | 51 | 33 |
| 1/200 | 523 | 51 | 87 |

(>: optical density greater than 2000)

The results are expressed in OD×10$^3$ (optical density at λ=450 nm).

Key: 20111 (225): anti-human type I collagen
50121 (03): anti-bovine type I collagen
50171 (01): anti-fish (sole) type I collagen This Table of results shows that, irrespective of the antibody (anti-human type I collagen, anti-bovine type I collagen, anti-sole type I collagen) in immunolabeling, the difference between human collagen and sole collagen is much greater than between human collagen and bovine collagen. Consequently, in a fish collagen matrix, the collagen synthesized by human fibroblasts may be identified much more easily. This confirms the results described above which were obtained by immunolabeling collagen synthesized in the fish collagen matrix with the anti-human type I collagen antibody, constituting a particularly unexpected and advantageous result of the invention.

What is claimed is:

1. A method of in vitro testing of the efficacy of a potentially active substance comprising monitoring the effect of said potentially active substance on an artificial skin comprising a composite product forming a collagen support comprising at least one porous collagen layer covered on at least one side with a collagen membrane component selected from the group consisting of a collagen membrane prepared by a compression of a collagen sponge at a pressure of at least about 50 bar and a collagen membrane comprising a collagen film prepared by drying a collagen gel separately from the porous collagen layer; and evaluating the monitored effect to determine selection or non selection of said substance as an efficient active substance.

2. The method of claim 1, wherein at least one of the porous layer and of the collagen membrane component comprises living cells selected from the group consisting of normal living cells, genetically modified living cells and malignant living cells.

3. The method of claim 1, wherein at least one of the porous layer and of the collagen membrane component comprises living cells originating from young subjects.

4. The method of claim 1, wherein at least one of the porous layer and of the collagen membrane component comprises living cells originating from elderly subjects.

5. The method of claim 1, wherein at least one of the porous layer and of the collagen membrane component comprises living cells selected from the group consisting of fibroblasts, keratinocytes, melanocytes, Langerhans' cells originating from the blood, endothelial cells originating from the blood, blood cells, sebocytes, chondrocytes, osteocytes, osteoblasts, nervous cells, Merkel's cells and dendritic cells, said cells being normal, genetically modified or malignant.

6. The method of claim 1, wherein said collagen of at least one of the collagen porous layer and of the collagen membrane component is of aquatic origin.

7. The method of claim 1, wherein said collagen support comprises:
a porous collagen layer prepared from a collagen gel of aquatic origin covered on at least one side with said collagen membrane component.

8. The method of claim 6, wherein said collagen gel of aquatic origin is obtained from fish skin.

9. The method of claim 7, wherein said collagen gel of aquatic origin is obtained from fish skin in its native form.

10. The method of claim 1, wherein said porous collagen layer is prepared from aquatic collagen gel which has undergone a lyophilization step, and wherein said porous collagen layer has its mechanical strength or its resistance to enzymatic digestion increased by a physical crosslinking.

11. The method of claim 1, wherein at least one of the porous collagen layer and of the collagen membrane component comprises a compound which favours cell development.

12. The method of claim 11, wherein said compound which favours cell development is selected from the group consisting of a growth factor, cytokine and a chemokine.

13. The method of claim 2, wherein said living cells originate essentially from human subjects.

14. The method of claim 13, wherein said living cells are selected from the group consisting of fibroblasts, keratinocytes, melanocytes, Langerhans' cells originating from the blood, endothelial cells originating from the blood, Merkel's cells originating from the blood, blood cells, adipocytes, sebocytes, chondrocytes, osteocytes, osteoblasts, dendritic cells and combinations thereof.

15. The method of claim 14, wherein said blood cells are macrophages, lymphocytes, or combinations thereof.

16. The method of claim 13, wherein said porous collagen layer comprises normal, genetically modified or malignant fibroblasts, and wherein said collagen membrane component comprises normal, genetically modified or malignant living cells selected from the group consisting of keratinocytes, melanocytes, Merkel's cells originating from the blood, Langerhans'cells originating from the blood, sebocytes cells originating from the blood, nerve cells, dendritic cells and combinations thereof.

17. The method of claim 1, wherein said collagen is mixed with a polysaccharide selected from the group consisting of a glycosaminoglycan, chitosan, a cellulose, dextran, an alginate, a carrageenan, and mixture thereof.

18. The method of claim 1, wherein the collagen film of the collagen membrane component is prepared by drying the collagen gel in air.

19. The method of claim 18, wherein after having prepared the collagen membrane component comprising the collagen film, the collagen gel is deposited on at least one surface of the collagen membrane component and the combination of the collagen gel with the collagen membrane component is frozen and lyophilised to give said composite product.

20. The method of claim 1, wherein at least one of the porous layer and of the collagen membrane component is produced from a collagen gel containing a mixture of soluble collagen and insoluble collagen.

21. The method of claim 20, wherein said insoluble collagen comprises collagen fibers.

22. The method of claim 1, wherein at least one of the porous layer and of the collagen membrane component is produced from a collagen gel containing a mixture of soluble collagen and insoluble collagen, wherein the collagen is selected from the group consisting of type I collagen and type III collagen.

23. The method of claim 1, wherein the porous layer comprises living cells selected from the group consisting of fibroblasts, dendritic cells, blood cells, macrophages or lymphocytes, adipocytes, sebocytes, chondrocytes, osteocytes, osteoblasts and nervous cell, and Merkel's cells originating from the blood, and said collagen membrane component comprises living cells selected from the group consisting of keratinocytes, melanocytes, Langerhans cells originating from the blood, endothelial cells originating from the blood, blood cells and Merkel's cells originating from the blood, dendritic cells said cells being normal, genetically modified or malignant.

24. A method of in vitro testing of the efficacy of potentially active substance comprising monitoring the effect of said potentially active substance on an artificial skin prepared from a composite collagen support comprising at least one porous collagen layer covered on at least one side with a collagen membrane comprising a collagen film prepared by drying a collagen gel in air separately from the porous collagen layer, said porous collagen layer comprising living fibroblasts cells and said collagen membrane comprising on a surface thereof living cells other than fibroblast; and evaluating the monitored effect to determine selection or non selection of said substance as an efficient active substance.

25. The method of claim 24, wherein said living cells on the surface of the membrane comprise keratinocytes.

26. The method of claim 24, wherein said porous collagen layer is prepared from a collagen gel of aquatic origin.

27. The method of claim 26, wherein said collagen gel of aquatic origin is obtained from fish skin.

28. The method of claim 26, wherein said collagen gel of aquatic origin is obtained from fish skin of a fish of the teleost family.

29. The method of claim 24, wherein at least one the porous collagen layer and of the collagen membrane is prepared from a flat fish skin.

30. The method of claim 24, wherein at least one of the porous collagen layer and of said collagen membrane is prepared from sole skin.

31. The method of claim 24, wherein said porous collagen layer is prepared from aquatic collagen gel which has undergone a lyophilization step, and wherein said porous collagen layer has its mechanical strength or its resistance to enzymatic digestion increased by a physical crosslinking.

32. A method of in vitro testing of the efficacy of a potentially active substance comprising monitoring the effect of said potentially active substance on an artificial skin prepared from a tissue engineering support comprising a porous collagen layer prepared from a collagen gel of aquatic origin; and a collagen membrane comprising a compressed collagen sponge, wherein said compression is carried out at a pressure of at least about 50 bar, wherein said porous collagen layer is covered on at least one side with said collagen membrane, and wherein at least one of said porous collagen layer and of said collagen membrane comprises living cells selecting from the group consisting of normal living cells, genetically modified living cells and malignant living cells; and evaluating the monitored effect to determine selection or non selection of said substance as an efficient active substance.

33. The method of claim 32, wherein said living cells originate from young subjects.

34. The method of claim 32, wherein said living cells originate from elderly subjects.

35. The method of claim 32, wherein said living cells originate from human subjects.

36. The method of claim 32, wherein said living cells are selected from the group consisting of fibroblasts, keratinocytes, melanocytes, Langerhans cells originating from the blood, endothelial cells originating from the blood, Merkel's cells, blood cells, adipocytes, sebocytes, chondrocytes, osteocytes osteoblasts, nervous cells, dendritic cells, and any combination thereof.

37. The method of claim 36, wherein said blood cells are macrophages, lymphocytes or any combination thereof.

38. The method of claim 1, wherein the collagen of at least one of said porous collagen layer and of said collagen membrane component is of aquatic origin and is derived from the skin of a fish selected from the group consisting of jellyfish, saltwater fish, freshwater fish, and combinations thereof.

39. The method of claim 1, wherein said collagen of at least one of said porous layer arid of said collagen membrane component is of aquatic origin and is derived from the skin of a flat fish.

40. The method of claim 32, wherein the collagen of at least one of said porous collagen layer and of said collagen membrane component is of aquatic origin and is derived from the skin of a fish selected from the group consisting of jellyfish, saltwater fish, freshwater fish, and combinations thereof.

41. The method of claim 32, wherein said collagen of at least one of said porous layer and of said collagen membrane component is of aquatic origin and is derived from the skin of a flat fish.

42. The method of claim 1, for simulating the effects of said potentially active substance on cell metabolism for the purpose of evaluating the efficacy and toxicity of raw materials or more complex formulations.

43. The method of claim 1, comprising measuring the efficacy of said potentially active substance in laminin production.

44. The method of claim 1, comprising evaluating the effect of fermented malt extract with regard to laminin production.

45. The method of claim 24, for simulating the effects of said potentially active substance on cell metabolism for the purpose of evaluating the efficacy and toxicity of raw materials or more complex formulations.

46. The method of claim 24, comprising measuring the efficacy of said potentially active substance in laminin production.

47. The method of claim 24, comprising evaluating the effect of fermented malt extract with retard to laminin production.

48. The method of claim 32, for simulating the effects of said potentially active substance on cell metabolism for the purpose of evaluating the efficacy and toxicity of raw materials or more complex formulations.

49. The method of claim 32, comprising measuring the efficacy of said potentially active substance in laminin production.

50. The method of claim 32, comprising evaluating the effect of fermented malt extract with regard to laminin production.

* * * * *